US006211345B1

(12) United States Patent
Weller et al.

(10) Patent No.: US 6,211,345 B1
(45) Date of Patent: Apr. 3, 2001

(54) SYNTHESIS OF CYCLIC SULFUR SILANES

(75) Inventors: Keith J. Weller, Yonkers; Lesley Hwang, Ossining, both of NY (US)

(73) Assignee: Witco Corporation, Greenwich, CT (US)

( * ) Notice: Subject to any disclaimer, the term of this patent is extended or adjusted under 35 U.S.C. 154(b) by 0 days.

(21) Appl. No.: 09/470,534

(22) Filed: Dec. 22, 1999

(51) Int. Cl.⁷ .................................................. C07F 7/08
(52) U.S. Cl. ................................... 532/427; 549/4
(58) Field of Search ................. 556/427; 549/4

(56) References Cited

U.S. PATENT DOCUMENTS

| | | | |
|---|---|---|---|
| 3,451,458 | 6/1969 | Stueber | 152/330 |
| 3,664,403 | 5/1972 | Doran et al. | 152/330 |
| 3,768,537 | 10/1973 | Hess et al. | 152/330 |
| 3,884,285 | 5/1975 | Russell et al. | 152/330 |
| 3,938,574 | 2/1976 | Burmester et al. | 152/330 |
| 4,100,172 * | 7/1978 | Mui et al. | 556/427 X |
| 4,128,438 | 12/1978 | Wolff et al. | 106/307 |
| 4,482,663 | 11/1984 | Kraus | 524/99 |
| 4,519,430 | 5/1985 | Ahmad | 152/209 |
| 4,590,052 | 5/1986 | Chevallier et al. | 423/335 |
| 4,704,414 | 11/1987 | Kerner et al. | 523/213 |
| 5,066,721 | 11/1991 | Hamada et al. | 525/102 |
| 5,089,554 | 2/1992 | Bomo et al. | 524/493 |
| 5,110,969 | 5/1992 | Dittrich et al. | 556/327 |
| 5,227,425 | 7/1993 | Rauline | 514/493 |
| 5,753,732 | 5/1998 | Wideman et al. | 524/263 |

FOREIGN PATENT DOCUMENTS 1424503 2/1976 (GB).

OTHER PUBLICATIONS

Bartlett, P.D. and Ghosh, T., Journal of Organic Chemistry, 1987, 52, 4937.

Shields, T.C. and Kurtz, A.N., Journal of the American Chemical Society, 1969, 91, 5415.

Leste–Lasserre, P., Harpp, D. N. *Sulfur allotrope chemistry*—$S_{10}$ an effective two–sulfur transfer reagent, Tetrahedron Letters 40 (1999), pp. 7961–7964.

Sato, R., Kimura, T., Goto, T., Saito, M. Synthesis and Reactions of New Cyclic Polysulfides. 6,10–disubstituted[1,2,3]trithiolo[5,4–H]benzopentathiepins, Tetrahedron Letters, vol. 29, No. 48 (1988), pp. 6291–6294.

Sato, R., Kimura, T., Goto, T., Saito, M., Kabuto, C. First Direct Synthesis of 4,8–Dialkylbenzo[1,2–d;4,5–d']bis[1,2,3]trithioles and 6, 10–Dialkyl[1,2,3]trithiolo[5,4–h]benzopentatiepins from 1,4–Dialkyl–2,3,5,6–tetrabromobenzenes, Tetrahedron Letters, vol. 30, No. 26, (1989), pp. 3453–3456.

Bartlett, P. D., Ghosh, T. *Sulfuration of the Norbornene Double Bond*, J. Org. Chem., vol. 52 (1987), pp. 4937–4943.

* cited by examiner

*Primary Examiner*—Paul F. Shaver
(74) *Attorney, Agent, or Firm*—Shirley S. Ma

(57) ABSTRACT

Sulfur-containing norbornanyl silanes are prepared in a simple, solventless manner by the reaction of a norbornenylsilane with sulfur in the presence of a chlorosilane. The resulting silanes may be used without further purification. The silanes were found to give good properties in rubber compositions for low-rolling-resistance tire applications.

10 Claims, No Drawings

SYNTHESIS OF CYCLIC SULFUR SILANES

BACKGROUND OF THE INVENTION

The invention relates to preparation of certain cyclic sulfur silanes in a simple, solventless manner. In its more preferred aspects, it provides silanes that can be used without further purification for applications such as coupling agents in rubber for making tires exhibiting reduced rolling resistance.

Rubber compositions for tire treads have traditionally employed carbon black as a principal reinforcing filler. Recently, as demands for fuel efficiency and performance have increased, the use of silica instead of carbon black as a principal filler has become more prevalent. In some cases, the use of silica in tire treads has been found to give lower rolling resistance without sacrificing abrasion resistance, modulus, or wet traction. However, in order for silica to be an effective reinforcing filler, a coupling agent is required. In this regard, see U.S. Pat. Nos. 3,451,458; 3,664,403; 3,768,537; 3,884,285; 3,938,574; 4,482,663; 4,519,430; 4,590,052; 5,066,721; 5,089,554; and 5,753,732 and British Patent No. 1,424,503. The coupling agents most often used in practice are polysulfide silanes of a type such as Silquest® A-289 silane, which is a bis-3-(triethoxysilylpropyl) tetrasulfide silane, or Silquest® A-1589 silane, which is a bis-3-(triethoxysilylpropyl)disulfide silane.

There is a need for other types of silanes that can give improvements in rolling resistance without having a detrimental impact on other properties. Norbornanylsulfursilanes, or trithiane silanes, are known for use in some applications as coupling agents, although not in tire rubber compositions for treads where their properties are unknown. See, for example, U.S. Pat. No. 4,100,172 to Mui, J. Y. P. and Kanner B., assigned to Union Carbide Corporation, New York, 1978. The previously published syntheses of cyclic sulfur silanes are disadvantageous, because they involve the use of ammonia gas as a base, and large quantities of solvent. Shields, T. C. and Kurtz, A. N., Journal of the American Chemical Society, 1969, 91, 5415, and Bartlett, Paul D. and Ghosh, Tirthankar, Journal of Organic Chemistry, 1987, 52, 4937. Its manufacturing process is therefore impractical and uneconomical due to the problems associated with the handling of a dangerous gas and the cost associated with the recovery or disposal of the solvent.

There remains a need for a process that can simply and efficiently prepare certain cyclic sulfur silanes without the use of solvents, reduces the need to handle dangerous materials, provides increased pot yields and ideally eliminates the need for further purification.

BRIEF DESCRIPTION OF THE INVENTION

It is an object of the invention to provide an improved process for the synthesis of episulfide, dithiane, trithiane, tetrathiane and pentathiane silanes (collectively, "Cyclic Sulfur Silanes").

It is another object of the invention to provide an improved process for the synthesis of Cyclic Sulfur Silanes which reduces the need to handle dangerous materials.

It is another object of the invention to provide an improved process for the synthesis of Cyclic Sulfur Silanes which eliminates the need for solvents.

It is another object of the invention to provide an improved process for the synthesis of Cyclic Sulfur Silanes which increases pot yields.

It is another object of the invention to provide an improved process for the synthesis of Cyclic Sulfur Silanes which produces a reaction mixture that can be used without further purification.

It is still another object of the invention to provide a process by which one can simply and efficiently prepare Cyclic Sulfur Silanes without the use of solvents, the need to handle dangerous materials is decreased, increased pot yields are provided and ideally the need for further purification is eliminated.

These and other objects are achieved by the present invention, which provides a process for preparing sulfur containing norbornanyl silicon compounds characterized by the structure

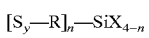
$$[S_y\text{—}R]_n\text{—}SiX_{4-n}$$

wherein each X is chosen from monovalent hydrocarbon groups or hydrolyzable groups, including, but not limited to, alkoxy, halide or an oxygen, which oxygen in turn is bonded to another silicon atom to form a siloxane; y is 1 to 5, when y is 1 the compound is an episulfide, and when y is 2 to 5 the sulfur atoms form a polysulfide wherein each sulfur atom is bonded to another sulfur atom and the terminal valences of the polysulfide are bonded to vicinal carbon atoms; n is 1, 2 or 3; R is a polyvalent polycycloaliphatic hydrocarbon radical, the process comprising:

reacting sulfur with an unsaturated silicon compound of the formula

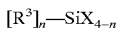
$$[R^3]_n\text{—}SiX_{4-n}$$

where $R^3$ is a polycycloaliphatic group containing at least one reactive strained double bond and X is as defined for Formula I above, the sulfur and silicon compound being reacted in the presence of an acid catalyst.

The unpurified products prepared in the above manner are unique in composition and properties.

Many of the preferred aspects of the invention are described below.

DETAILED DESCRIPTION OF THE INVENTION

The following description will illustrate the preparation of preferred norbornanyl silicon compounds, suitable for use as coupling agents for low rolling resistance tire applications. The invention is, however, not limited to the specific compounds illustrated or this particular use.

This invention relates to the improved synthesis of sulfur containing norbornanyl silicon compounds characterized by the following structure (Formula I):

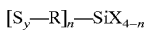
$$[S_y\text{—}R]_n\text{—}SiX_{4-n} \qquad \text{(Formula I)}$$

wherein each X is chosen from monovalent hydrocarbon groups, or hydrolyzable groups, including, but not limited to alkoxy, halide or an oxygen which oxygen in turn is bonded to another silicon atom to form a siloxane; y is 1 to 5, when y is 1 the compound is an episulfide, and when y is 2 to 5 the sulfur atoms form a polysulfide wherein each sulfur atom is bonded to another sulfur atom and the terminal valences of the polysulfide are bonded to vicinal carbon atoms; n is 1, 2 or 3; R is a polyvalent polycycloaliphatic hydrocarbon radical including but not limited to

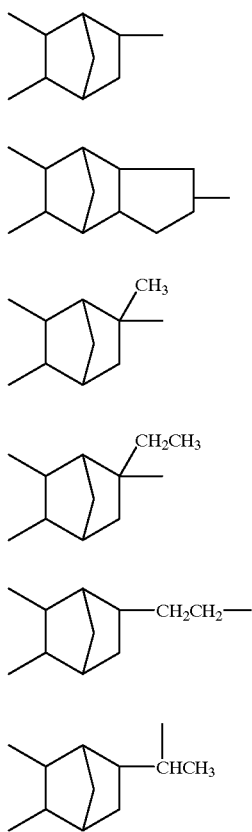

(a)

(b)

(c)

(d)

(e)

(f)

In the above structures, the valencies to the left would be connected to the sulfur so as to form a ring and the valency to the right would be connected to the silicon atom.

Each X may be the same or different. Among the hydrocarbon groups for X are alkyl groups, preferably lower alkyls including from one to four carbons. Among the hydrolyzable X groups are halides, such as chlorine, siloxies, such as trimethoxysiloxy or methyltriethoxysiloxy, the lower alkoxy groups, preferably those containing from one to four carbons. Mixed alkoxy groups (e.g., one being methoxy and another being ethoxy are a potential embodiment. In one embodiment, the silane may be a dimer of the Cyclic Sulfur Silane, such that the siloxy group is another alkoxy silane containing the sulfur group, e.g., 1,3-bis[(ethyl)-2-(3,4,5-trithiatricyclo[5.2.1.0$^{2.6}$]decyl)]tetraethoxy disiloxane. The most preferred X groups are ethoxy and methoxy.

Y is preferably 1, 3 or 5, more preferably 1 or 3.

The group R can be derived from a variety of polycycloaliphatic compounds containing at least one reactive, strained double bond, such as those represented by Formulas II, III and IV, as follows:

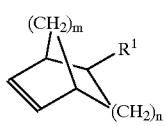

(Formula II)

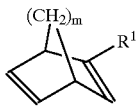

(Formula III)

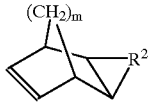

(Formula IV)

Where m=1 or 2, n=0 to 8, $R^1$ is selected from the group of H, $C_1$–$C_{12}$ alkyl, or $C_2$–$C_{12}$ alkenyl and $R^2$ is a $C_2$–$C_4$ alkene.

Non-limiting examples of the above compounds of Formulas II, III and IV are preferably selected from the group g–k:

(g)

(h)

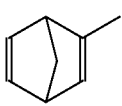

(i)

(j)

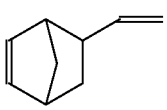

(k)

The sulfur-substituted polycycloaliphatic compounds of this invention, as characterized by Formula I, can be produced by the reaction of sulfur from any suitable source with an aliphatically unsaturated precursor of the silicon compound according to Formula Va in the presence of an acid catalyst. Among the suitable sources of sulfur are any of those that are capable of providing sulfur for the reaction under conditions effective to produce the desired products, e.g., any of the allotropes of elemental sulfur, or a compound capable of donating free sulfur, such as, but not limited to, di-n-hexadecyl tetrasulfide, di-carboxymethyl tetrasulfide, dimethyl hexasulfide, bis-(dimethylthiocarbamyl) hexasulfide and bis(triethoxysilylpropyl)tetrasulfide. It is preferred that the sulfur source be essentially free of water and more preferably, absolutely free of water. Suitable unsaturated silicon compounds are defined as follows:

$$[R^3]_n\text{—}SiX_{4-n} \quad \text{(Formula Va)}$$

where $R^3$ is a polycycloaliphatic group containing at least one reactive strained double bond and X is as defined for Formula I above. Exemplary of the R³ groups for the precursor compounds are groups l through q, as follows:

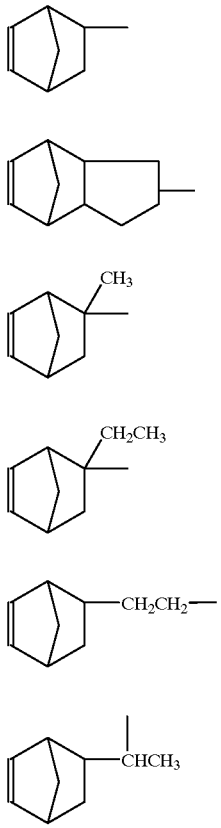

The synthesis of compounds of Formula Va may be made by several routes, preferably by hydrosilation of a compound containing two double bonds such as, but not limited to, those compounds g to k, or from the Diels-Alder type reaction of a vinyl-containing silane with a suitable diene, such as but not limited to, cyclopentadiene, methylcyclopentadiene, dicyclopentadiene and methylcyclopentadiene dimer.

Suitable acid catalysts include common organic acids, such as acid chlorides like acetyl chloride, or inorganic acids, such as hydrochloric. However, the acid will preferably be a silicon compound of Formula Vb containing at least one Si—Cl bond, referred to herein as chlorosilanes, as follows:

$$[R^3]_n\text{—SiX}_{4-n} \quad \text{(Formula Vb)}$$

The most preferred compounds are chlorosilanes of Formula Vb wherein at least one of X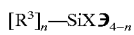 is occupied by a halogen, preferably chlorine, and the remainder are as defined for X, and R³ is a polycycloaliphatic group containing at least one reactive strained double bond as described above.

A typical example of this reaction is shown in Equation I, as follows:

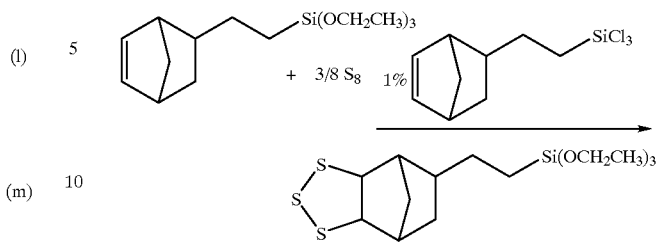

(Equation I)

The reaction may be performed without any solvent, but solvents can be employed where they add practical value to the process. The product can be distilled, but in general, this is not necessary, since the reaction proceeds cleanly and in high yield. Among the available solvents are aromatic and aliphatic hydrocarbons, alcohols, ketones and ethers. Among the aromatic hydrocarbons are xylene, toluene, and benzene. Among the aliphatic hydrocarbons are pentane, hexane, octane, isooctane, decane, cyclohexane and methylcyclohexane. Among the alcohols are methanol, ethanol, isopropanol, propanol, butanol, hexanol, octanol and t-butanol. The ketones are represented by methyl ethyl ketone, methyl isopropyl ketone and cyclohexanone. The ethers are represented by tetrahydrofuran, dioxane, dioxolane and glyme. Certain of the solvents with low boiling points might require performing the reaction under elevated pressure. The solvent may be present at 0 to 90 weight percent, more preferably 0 to 50 weight percent.

A general procedure for the synthesis of the sulfur containing norbomanyl silanes of Formula I will entail directly reacting with sulfur, a norbornenylsilane of Formula Va in the presence of a chlorosilane catalyst, in a molar ratio in the range of about 1000:1 to about 10:1. The molar ratio of the norbomenylsilane of formula Va to moles sulfur in the sulfur source will be about 1:3 to about 1:4. The reaction temperature is advantageously over 150° C., preferably between 10 150° C. and 200° C. Preferably, the molar ratio of the norbornenylsilane of formula Va to chlorosilane is in the range of about 1000:1 to about 100:1. The process can be performed at any reaction pressure near ambient, preferably from 0.8–1.2 atmospheres. Again, the use of low-boiling solvents may require the use of elevated pressures. The exclusion of water from the reaction by the use of a drying agent in a drying tube, or by the use of inert gases such as nitrogen or argon is the preferred method of the present invention.

Non-limiting examples of compounds of Formula I are shown below:

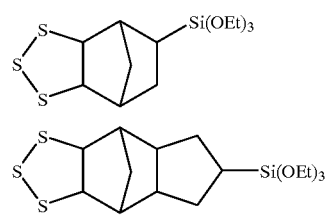

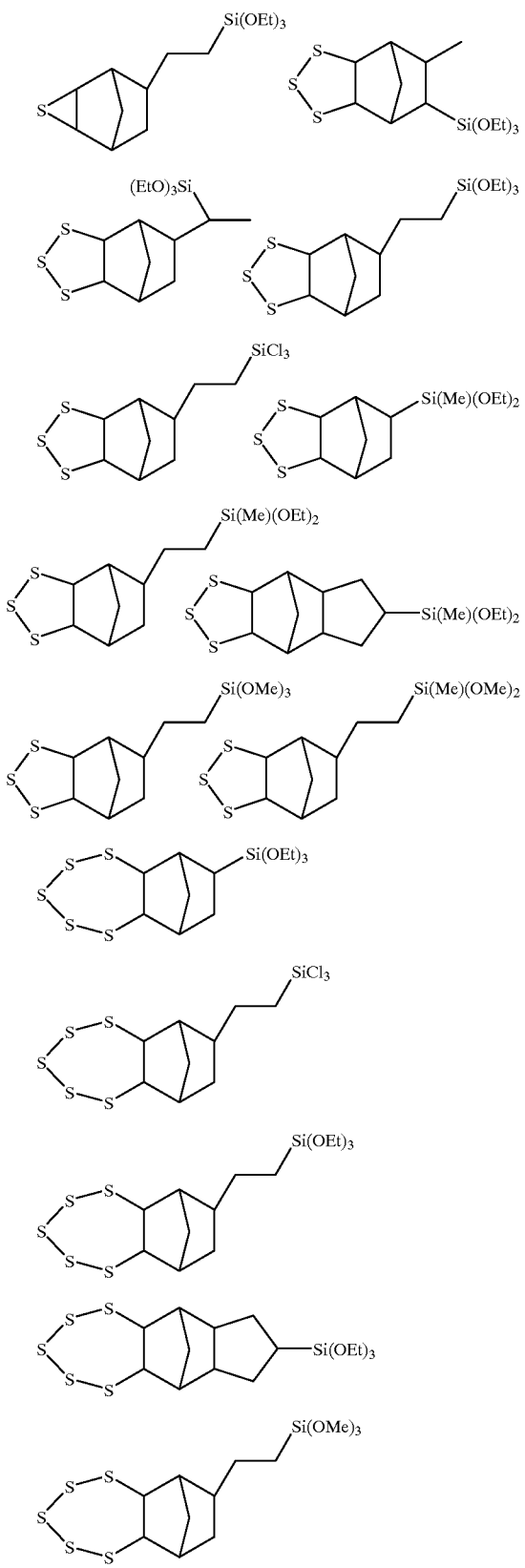

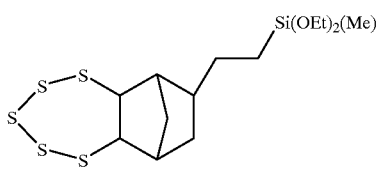

The product Cyclic Sulfur Silanes of the invention can be directly recovered from the reaction mixture, such as by decanting and/or filtering, if desired. The product will typically have a dark color if no treatment is undertaken, but color and impurities present will not affect its use in rubber compounds. If desired, the color can be improved by vacuum distillation to produce a light yellow liquid. It is an advantage of the invention that the products can be utilized in the form as recovered, without the use of additional purification for prior art uses of materials of this type. In addition, new uses such as for preparing tire rubber compositions utilizing silica reinforcing fillers can also be accomplished without detrimental effect caused by the unpurified product Cyclic Sulfur Silanes or their component impurities.

The Cyclic Sulfur Silane compositions of the invention can be used in the manner of the products of U.S. Pat. No. 4,100,172, which is hereby incorporated by reference in its entirety. They can also be used as coupling agents for "silica-reinforced rubber" compositions, suitable for uses such as tires, as described in copending application entitled "Use Of Cyclic Sulfur Silanes As Coupling Agents In Sulfur-Vulcanizable, Silica-Reinforced Tire Rubber Compositions" (attorney's docket no. 2062-SIL0046USE) filed in the name of Keith J. Weller on the same date as this application. The full disclosure of this copending application is also incorporated by reference.

The Cyclic Sulfur Silane compositions of the invention can be employed in natural and synthetic rubber compositions and blends of known and novel formulation, in amounts consistent with those previously employed for the above and other uses. Exemplary of suitable rubber compositions are sulfur-vulcanizable synthetic rubber compositions, including styrene butadiene rubbers (SBR) prepared by either solution or emulsion polymerization procedures. See, for example, U.S. Pat. No. 3,451,458, U.S. Pat. No. 5,110,969, U.S. Pat. No. 5,227,425 and U.S. Pat. No. 5,753,732 for examples of rubber compounds that can be improved with the invention with silica as a reinforcing agent. The disclosures of these patents are incorporated by reference in their entireties.

The rubber compositions, in addition to elastomers of synthetic or natural origin, can contain silica in amounts effective for reinforcing the rubber in its vulcanized state. The silica can be of the types known, for example described in U.S. Pat. No. 4,704,414, U.S. Pat. No. 5,227.425 and U.S. Pat. No. 5,753,732, and will be employed in amounts suitable for the intended product. In the case of tires, especially those having low rolling resistance, the silica will be employed at a level of from about 5 to about 100 parts per hundred parts by weight of rubber preferably at least 30 parts silica on this basis. Higher or lesser amounts can be employed where appropriate. The "silica-reinforced rubber" compositions as can be improved by the invention do not exclude the presence of carbon black which will still be present as a preferred ingredient in minor amounts for purposes of coloring or as a carrier for additives, even including the silane coupling agents. In this latter regard, see U.S. Pat. No. 4,128,438 and U.S. Pat. No. 5,159.009, which are incorporated by reference in their entireties. The silica component will, however preferably be present in an amount greater than the carbon black in tires or tire rubber compounds.

The following Examples are provided to further illustrate and explain a preferred form of the invention and are not to be taken as limiting in any regard. Unless otherwise indicated, all parts and percentages are by weight.

EXAMPLE I

Preparation of 8-(2-triethoxysilyl)ethyl-3,4,5-trithiatricyclo[5.2.1.0$^{2.6}$]decane Into a 250 ml round bottomed flask equipped with magnetic stir bar, condensor, thermocouple, heating mantle, and $N_2$ inlet was charged 2-(5-norbornenyl)-ethyltriethoxysilane (100.0 g, 0.35 moles), $S_8$ (33.8 g, 1.05 moles), and 2-(3-cyclohexenyl)-ethyltrichlorosilane (1.5 ml, approximately I mole % based on silane). The contents of the flask were heated to 160° C. for 3 hours, then allowed to cool to room temperature. The resulting dark liquid was filtered through a 0.5-micron filter using a pressure filter apparatus. The filtrate weighed 125.9 g, giving a yield of 94%. The product, 8-(2-triethoxysilyl)ethyl-3,4,5-trithiatricyclo[5.2.1.0$^{2.6}$]decane, was identical by GC and GC/MS to that produced by the method detailed in U.S. Pat. 4,100,172, as detailed below.

COMPARATIVE EXAMPLE—from U.S. Pat. 4,100,172

Preparation of 8-(2-trimethoxysilyl)ethyl-3,4,5-trithiatricyclo[5.2.1.0$^{2.6}$]decane.

Into a 2-liter three-necked flask equipped with a mechanical stirrer, a condenser and a thermometer were charged 1230 grams of N, N-dimethyl formamide (DMF) and 236 grams of sulfur flower. The contents were stirred and ammonia gas from a cylinder was bubbled into the mixture at 61 ml/minute for 20 minutes (total 1220 ml or 0.49 mole). Then, 491.5 grams (2.29 mole) of trimethoxynorbornenyl-silane were added and the contents were heated to 110° C. for 2 hours. The contents were cooled to 60° C and the solvent, dimethyl formamide (DMF), was stripped under vacuum. Essentially quantitative recovery of DMF (1228 grams) was observed. Weight of crude product was 724 grams, amounting to about 100% yield of 8-(2-trimethoxysilyl)ethyl-3,4,5-trithiatricyclo[5.2.1.0$^{2.6}$decane.

The above description is intended to enable the person skilled in the art to practice the invention. It is not intended to detail all of the possible modifications and variations which will become apparent to the skilled worker upon reading the description. It is intended, however, that all such modifications and variations be included within the scope of the invention which is defined by the following claims. The claims are meant to cover the indicated elements and steps in any arrangement or sequence which is effective to meet the objectives intended for the invention, unless the context specifically indicates the contrary.

What is claimed is:

1. A process for preparing a reaction mixture containing a sulfur containing norbornanyl silicon compound characterized by the following structure (Formula I):

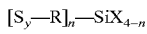
$[S_y—R]_n—SiX_{4-n}$    Formula I wherein each X is chosen from monovalent hydrocarbon groups or hydrolyzable groups; y is 1 to 5, when y is 1 the compound is an episulfide, and when y is 2 to 5 the sulfur atoms form a polysulfide wherein each sulfur atom is bonded to another sulfur atom and the terminal valences of the polysulfide are bonded to vicinal carbon atoms; n is 1, 2 or 3; R is a polyvalent polycycloaliphatic hydrocarbon radical, the process comprising:

reacting sulfur with an unsaturated silicon compound of the formula

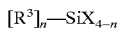
$[R^3]_n—SiX_{4-n}$    (Formula Va)

where $R^3$ is a polycycloaliphatic group containing at least one reactive strained double bond and each X is as defined for Formula I above, the sulfur and silicon compound being reacted in the presence of an acid catalyst.

2. A process according to claim 1, wherein $R^3$ is a member selected from the group consisting of:

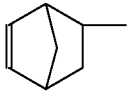
(l)

(m)

(n)

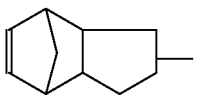
(o)

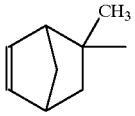

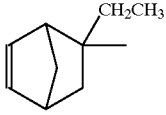
(p)

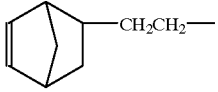

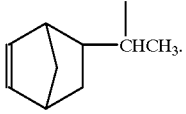
(q)

3. A process according to claim 1 wherein the catalyst comprises a chlorosilane.

4. A process according to claim 1 wherein the chlorosilane is defined by the following formula:

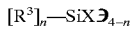
$[R^3]_n—SiӘ_{4-n}$    (Formula Vb)

wherein at least one of XӘ is occupied by a halogen, and the remainder are as defined for X, and $R^3$ is a polycycloaliphatic group containing at least one reactive strained double bond.

5. A process according to claim 4 wherein $R^3$ is a member selected from the group consisting of:

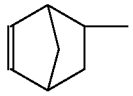 (l)

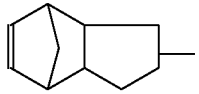 (m)

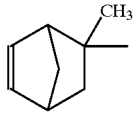 (n)

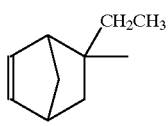 (o)

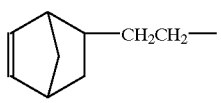 (p)

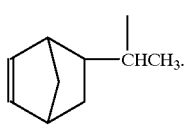 (q)

6. A process for preparing a reaction mixture containing a sulfur-containing norbornenyl silicon compound of the formula

[S_y—R]_n—SiX_{4-n}   (Formula I)

wherein each X is chosen from monovalent hydrocarbon groups, or hydrolyzable groups, y is 1 to 5, when y is 1 the compound is an episulfide, and when y is 2 to 5 the sulfur atoms form a polysulfide wherein each sulfur atom is bonded to another sulfur atom and the terminal valences of the polysulfide are bonded to vicinal carbon atoms; n is 1, 2 or 3; R is a polyvalent polycycloaliphatic hydrocarbon radical, the process comprising:

heating a mixture of an unsaturated silicon compound of the formula

[R³]_n—SiX_{4-n}   (Formula Va)

where $R^3$ is a polycycloaliphatic group containing at least one reactive strained double bond and each X is as defined for Formula I above, the sulfur and silicon compound being reacted in the presence of an acid catalyst defined by the formula

[R³]_n—SiX3_{4-n}   (Formula Vb)

wherein at least one of X3 is occupied by a halogen, and the remainder are as defined for X, and $R^3$ is a polycycloaliphatic group containing at least one reactive strained double bond;

wherein the molar ratio of the unsaturated silicon compound to chlorosilane is within the range of from 1000:1 to 10:1 and the molar ratio of unsaturated silane to elemental sulfur is within the range of from 1:3 to 1:4.

7. A process according to claim 6 wherein R is selected from the group consisting of

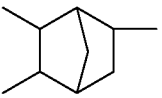 (a)

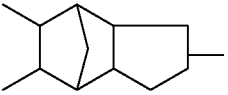 (b)

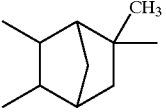 (c)

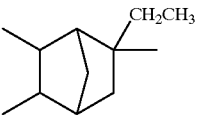 (d)

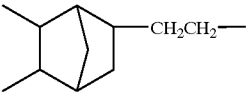 (e)

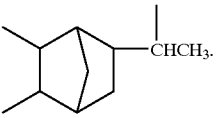 (f)

8. A process according to claim 6 wherein the hydrolyzable group is chlorine.

9. A process according to claim 6 wherein the reaction is conducted at a temperature above 150° C. at a pressure near ambient.

10. A process according to claim 6 including the further step of distilling the reaction mixture.

* * * * *